United States Patent
Thompson et al.

(10) Patent No.: US 7,727,755 B2
(45) Date of Patent: Jun. 1, 2010

(54) ENZYME AND METHODOLOGY FOR THE TREATMENT OF A BIOMASS

(75) Inventors: Vicki S. Thompson, Idaho Falls, ID (US); David N. Thompson, Idaho Falls, ID (US); Kastli D. Schaller, Ammon, ID (US); William A. Apel, Jackson, WY (US)

(73) Assignee: Battelle Energy Alliance, LLC, Idaho Falls, ID (US)

( * ) Notice: Subject to any disclaimer, the term of this patent is extended or adjusted under 35 U.S.C. 154(b) by 530 days.

(21) Appl. No.: 11/266,063

(22) Filed: Nov. 2, 2005

(65) Prior Publication Data

US 2007/0099282 A1  May 3, 2007

(51) Int. Cl.
 *C12N 9/42* (2006.01)
(52) U.S. Cl. .................. 435/209; 435/41; 435/161
(58) Field of Classification Search .............. 435/41, 435/161, 209
 See application file for complete search history.

(56) References Cited

U.S. PATENT DOCUMENTS

| 5,882,905 | A | * | 3/1999 | Saha et al. | ............. 435/105 |
| 5,916,795 | A | | 6/1999 | Fukunaga et al. | |
| 5,948,667 | A | * | 9/1999 | Cheng et al. | ............. 435/200 |
| 6,083,733 | A | | 7/2000 | Grönberg et al. | |
| 6,268,197 | B1 | | 7/2001 | Schulein et al. | |
| 6,426,211 | B1 | | 7/2002 | De Buyl et al. | |
| 6,506,585 | B2 | | 1/2003 | Danielsen et al. | |
| 6,777,212 | B2 | | 8/2004 | Asakura et al. | |
| 6,833,259 | B2 | | 12/2004 | Bhosle et al. | |
| 2003/0134395 | A1 | | 7/2003 | Shetty | |
| 2005/0112742 | A1 | | 5/2005 | Thompson et al. | |

FOREIGN PATENT DOCUMENTS

WO  WO 03/068926 A2 *  8/2003

OTHER PUBLICATIONS

Ito, K et al. Purification and properties of acid stable xylanases from *Aspergillus kawachii*. Biosci. Biotech. Biochem. 1992. 56(4): 547-550.*
T. Collins et al., "Xylanases, Xylanase Families and Extremophilic Xylanases", FEMS Microbiology Review, 2005, pp. 3-23.
K. Eckert et al., "A Thermoacidophilic Endoglucanase (CelB), etc.," Eur. J. Biochem. 270, 2003, pp. 3593-3602.
International Application Published Under the Patent Cooperation Treaty, Wo 2005/066339, Wilting et al, published Jul. 21, 2005.
International Preliminary Report on Patentability and Written Opinion of the International Searching Authority for PCT/US06/42566 Apr. 23, 2009 (7 pages).
Supplemental European Search Report for EP 06 82 7231, dated Nov. 12, 2009, 6 pages.
Shallom et al., "Microbial hemicellulases," Current Opinion in Microbiology, Current Biology Ltd, GB, vol. 6, No. 3, Jun. 1, 2003, pp. 219-228.
Eckert et al., "Gene cloning, sequencing, and characterization of a family 9 endoglucanase (CeIA) with an unusual pattern of activity from the theremoacidophile *Alicyclobacillus acidocaldarius* ATCC27009," Applied Microbiology and Biotechnology, vol. 60, No. 4, Dec. 2002, pp. 428-436.

* cited by examiner

*Primary Examiner*—Leon B. Lankford, Jr.
*Assistant Examiner*—Susan E. Fernandez
(74) *Attorney, Agent, or Firm*—Traskbritt (57) ABSTRACT

An enzyme isolated from an extremophilic microbe, and a method for utilizing same is described, and wherein the enzyme displays optimum enzymatic activity at a temperature of greater than about 80° C., and a pH of less than about 2, and further may be useful in methodology including pretreatment of a biomass so as to facilitate the production of an end product.

20 Claims, 4 Drawing Sheets

SEQUENCE LISTING

```
<160> NUMBER OF SEQ ID NOS: 5

<210> SEQ ID NO 1
<211> LENGTH: 13
<212> TYPE: PRT
<213> ORGANISM: Alicyclobacillus acidocaldarius

<400> SEQUENCE: 1

Asp Val Val Ser Thr Pro Ile Ser Met Glu Ile Gln Val
1               5                   10

<210> SEQ ID NO 2
<211> LENGTH: 86
<212> TYPE: PRT
<213> ORGANISM: Alicyclobacillus acidocaldarius

<400> SEQUENCE: 2

Gln Ala Ser Ser Ser Ile Val Gly Asn Ala Leu Ala Gln Ala Ala Ser
1               5                   10                  15

Leu Ser Pro Thr Ile Ser Ala Tyr Leu Arg Gln Asn Gly Leu Ser Pro
                20                  25                  30

Ser Asp Leu Ala Arg Thr Trp Ser Ser Tyr Tyr Cys Thr Gln Phe Asp
            35                  40                  45

Asp Pro Gln Gly Ala Ala Gln Thr Ala Leu Ala Thr Arg Ile Cys Asn
        50                  55                  60

Asp Gln Ala Leu Gly Gly Gly Ala Pro Thr Ala Ser Ala Thr Ile Thr
65                  70                  75                  80

Val Asn Thr Ala Ala Arg
                85

<210> SEQ ID NO 3
<211> LENGTH: 47
<212> TYPE: PRT
<213> ORGANISM: Alicyclobacillus acidocaldarius

<400> SEQUENCE: 3

Gly Leu Asn Ala Ala Val Trp Asp Ser Gly Leu Asn Ser Gln Thr Val
1               5                   10                  15

Ile Ser Glu Val Gln Ala Leu His Pro Ala Leu Ile Arg Trp Pro Gly
                20                  25                  30

Gly Ser Ile Ser Asp Met Asp Tyr Asn Trp Glu Thr Asn Thr Arg
            35                  40                  45

<210> SEQ ID NO 4
<211> LENGTH: 39
<212> TYPE: PRT
<213> ORGANISM: Alicyclobacillus acidocaldarius
```

```
<400> SEQUENCE: 4

Glu Ala Asp Asp His Ala Val Pro Asn Gln Pro Gln Lys Gly Asn Pro
1               5                   10                  15

Gly Leu Ser Pro Gln Ala Tyr Ala Gln Asn Ala Leu Gln Phe Met Gln
            20                  25                  30

Ser Pro Val Val Tyr Tyr Arg
        35

<210> SEQ ID NO 5
<211> LENGTH: 959
<212> TYPE: PRT
<213> ORGANISM: Alicyclobacillus acidocaldarius

<400> SEQUENCE: 5

Met Lys Arg Pro Trp Ser Ala Ala Leu Ala Leu Ile Ala Leu Gly
1               5                   10                  15

Thr Gly Ala Ser Pro Ala Trp Ala Ala Ala His Pro Ser Pro Lys Val
            20                  25                  30

Pro Ala Gly Ala Ala Gly Arg Val Arg Ala Ala Asp Val Val Ser Thr
        35                  40                  45

Pro Ile Ser Met Glu Ile Gln Val Ile His Asp Ala Leu Thr Val Pro
    50                  55                  60

Glu Leu Ala Ala Val Gln Ala Ala Gln Ala Ala Ser Asn Leu Ser
65                  70                  75                  80

Thr Ser Gln Trp Leu Gln Trp Leu Tyr Pro Asn Ala Thr Pro Thr Thr
                85                  90                  95

Ser Ala Gln Ser Gln Ala Ala Gln Ala Val Ala Asn Leu Phe Asn Leu
            100                 105                 110

Ala Thr Tyr Gly Ala Val Ser Thr Arg Gly Ser Asn Ala Ala Gln Ile
        115                 120                 125

Leu Gln Thr Leu Gln Ser Ile Ser Pro Leu Leu Ser Pro Arg Ala Val
    130                 135                 140

Gly Leu Phe Tyr Gln Ser Phe Leu Thr Glu Ile Gly Gln Ser Ser Lys
145                 150                 155                 160

Ala Ile Leu Ala Arg Gln Ala Ser Ser Ile Val Gly Asn Ala Leu
                165                 170                 175

Ala Gln Ala Ala Ser Leu Ser Pro Thr Ile Ser Ala Tyr Leu Arg Gln
            180                 185                 190

Asn Gly Leu Ser Pro Ser Asp Leu Ala Arg Thr Trp Ser Ser Phe Glu
        195                 200                 205

Thr Gln Val Asp Pro Gln Gly Ala Ala Gln Thr Ala Leu Ala Thr Arg
    210                 215                 220

Ile Cys Thr Asn Ala Leu Gly Phe Gly Ala Pro Thr Ala Ser Ala Thr
225                 230                 235                 240

Ile Thr Val Asn Thr Ala Ala Arg Leu Arg Thr Val Pro Ala Thr Ala
                245                 250                 255

Phe Gly Leu Asn Ala Ala Val Trp Asp Ser Gly Leu Asn Ser Gln Thr
            260                 265                 270

Val Ile Ser Glu Val Gln Ala Leu His Pro Ala Leu Ile Arg Trp Pro
        275                 280                 285

Gly Gly Ser Ile Ser Asp Val Tyr Asn Trp Glu Thr Asn Thr Arg Asn
    290                 295                 300

Asp Gly Gly Tyr Val Asn Pro Asn Asp Thr Phe Asp Asn Phe Met Gln
305                 310                 315                 320
```

-continued

```
Phe Val Asn Ala Val Gly Ala Ser Pro Ile Ile Thr Val Asn Tyr Gly
            325                 330                 335

Thr Gly Thr Pro Gln Leu Ala Ala Asp Trp Val Lys Tyr Ala Asp Val
            340                 345                 350

Thr His His Asp Asn Val Leu Tyr Trp Glu Ile Gly Asn Glu Ile Tyr
            355                 360                 365

Gly Asn Gly Tyr Tyr Asn Gly Asn Gly Trp Glu Ala Asp Asp His Ala
            370                 375                 380

Val Pro Asn Gln Pro Gln Lys Gly Asn Pro Gly Leu Ser Pro Gln Ala
385                 390                 395                 400

Tyr Ala Gln Asn Ala Leu Gln Phe Ile Gln Ala Met Arg Ala Val Asp
                405                 410                 415

Pro Asn Ile Lys Ile Gly Ala Val Leu Thr Met Pro Tyr Asn Trp Pro
                420                 425                 430

Trp Gly Ala Thr Val Asn Gly Asn Asp Asp Trp Asn Thr Val Val Leu
            435                 440                 445

Lys Ala Leu Gly Pro Tyr Ile Asp Phe Val Asp Val His Trp Tyr Pro
            450                 455                 460

Glu Thr Pro Gly Gln Thr Asp Ala Gly Leu Leu Ala Asp Thr Asp
465                 470                 475                 480

Gln Ile Pro Ala Met Val Ala Glu Leu Lys Arg Glu Ile Asn Ala Tyr
                485                 490                 495

Ala Gly Ser Asn Ala Lys Asn Ile Gln Ile Phe Val Thr Glu Thr Asn
            500                 505                 510

Ser Val Ser Tyr Asn Pro Gly Gln Gln Ser Thr Asn Leu Pro Glu Ala
            515                 520                 525

Leu Phe Leu Ala Asp Asp Leu Ala Gly Phe Val Gln Ala Gly Ala Ala
            530                 535                 540

Asn Val Asp Trp Trp Asp Leu Leu Asn Gly Ala Glu Asp Asn Tyr Thr
545                 550                 555                 560

Ser Pro Ser Leu Tyr Gly Gln Asn Leu Phe Gly Asp Tyr Gly Leu Leu
            565                 570                 575

Ser Ser Gly Gln Ala Thr Pro Lys Gly Val Gln Glu Pro Pro Gln Tyr
            580                 585                 590

Thr Pro Leu Pro Pro Tyr Tyr Gly Phe Gln Leu Val Ser Asp Phe Ala
            595                 600                 605

Arg Pro Gly Asp Thr Leu Leu Gly Ser Ala Ser Gln Ser Asp Ile
            610                 615                 620

Asp Val His Ala Val Arg Glu Pro Asn Gly Asp Ile Ala Leu Met Leu
625                 630                 635                 640

Val Asn Arg Ser Pro Ser Thr Ile Tyr Ser Ala Asp Leu Asn Val Leu
            645                 650                 655

Gly Val Gly Pro Tyr Ala Ile Thr Lys Ala Leu Val Tyr Gly Glu Gly
            660                 665                 670

Ser Ser Ala Val Ser Pro Ala Leu Thr Leu Pro Thr Ala His Ser Val
            675                 680                 685

Lys Leu Met Pro Tyr Ser Gly Val Asp Leu Val His Pro Leu Ile
            690                 695                 700

Pro Ala Pro His Ala Ala Ser Val Thr Asp Thr Leu Ala Leu Ser
705                 710                 715                 720

Ser Pro Thr Val Thr Ala Gly Gly Ser Glu Thr Val Thr Ala Ser Phe
            725                 730                 735

Ser Ser Asp Arg Pro Val Arg Asp Ala Thr Val Glu Leu Glu Leu Tyr
```

```
                      740             745             750
Asp Ser Thr Gly Asp Leu Val Ala Asn His Glu Met Thr Gly Val Asp
        755                 760                 765

Ile Ala Pro Gly Gln Pro Val Ser Glu Ser Trp Thr Phe Ala Ala Pro
        770                 775                 780

Ala Ala Asn Gly Thr Tyr Thr Val Glu Ala Phe Ala Phe Asp Pro Ala
785                     790                 795                 800

Thr Gly Ala Thr Tyr Asp Ala Asp Thr Thr Gly Ala Thr Ile Thr Val
                805                 810                 815

Asn Gln Pro Pro Ala Ala Lys Tyr Gly Asp Ile Val Thr Lys Asn Thr
            820                 825                 830

Val Ile Thr Val Asn Gly Thr Thr Tyr Thr Val Pro Ala Pro Asp Ala
        835                 840                 845

Ser Gly His Tyr Pro Ser Gly Thr Asn Ile Ser Ile Ala Pro Gly Asp
        850                 855                 860

Thr Val Thr Ile Gln Thr Thr Phe Ala Asn Val Ser Ser Thr Asp Ala
865                 870                 875                 880

Leu Gln Asn Gly Leu Ile Asp Met Glu Val Asp Gly Gln Asn Gly Ala
                885                 890                 895

Ile Phe Gln Lys Tyr Trp Pro Ser Thr Thr Leu Leu Pro Gly Gln Thr
            900                 905                 910

Glu Thr Val Thr Ala Thr Trp Gln Val Pro Ser Ser Val Ser Ala Gly
        915                 920                 925

Thr Tyr Pro Leu Asn Phe Gln Ala Phe Asp Thr Ser Asn Trp Thr Gly
        930                 935                 940

Asn Cys Tyr Phe Thr Asn Gly Gly Val Val Asn Phe Val Val Asn
945                 950                 955
```

ENZYME AND METHODOLOGY FOR THE TREATMENT OF A BIOMASS

GOVERNMENT RIGHTS

This invention was made with government support under Contract No. DE-AC07-05ID14517 awarded by the United States Department of Energy. The government has certain rights in the invention.

TECHNICAL FIELD

The present invention relates to an enzyme and methodology for treatment of a biomass, more specifically to an enzyme that is water soluble, and further displays optimal enzymatic activity at a temperature of at least about 80° C., and at a pH of less than about 2.

BACKGROUND OF THE INVENTION

It has long been known that it would be desirable to utilize sugars contained in cellulose and hemicellulose of lignocellulosic residues for the production of fuels and value-added chemicals in bio-refinery arrangements. Lignocellulosic residues include such materials as corn stover that consists of a heterogeneous three-dimensional matrix comprised primarily of cellulose, hemicellulose and lignin. It has long been known that because of the heterogeneous nature of lignocellulose, the cellulose and hemicellulose are not directly accessible to relatively large molecules such as cellulase enzymes.

Heretofore, acid pretreatment processes have been developed to hydrolyze and remove hemicellulose, and thereby increase the susceptibility of the cellulose in the matrix to cellulolytic attack by cellulase enzymes. While this approach has worked with some degree of success, it is long been known that these acid pretreatment processes have high capital and operating costs due to high temperatures and pressures required, and further produce significant amounts of toxic decomposition products depending upon the pretreatment severity provided by the process. Another shortcoming attendant with this same approach is that these same thermal decomposition products represent a loss of potential sugars that could be utilized for subsequent fermentations.

Therefore, a method for treating a biomass, and an enzyme that when utilized with a treatment process that would reduce the severity of acid pretreatments, lower the energy and capital costs to allow increased yields of hemicellulose-derived sugars and minimize the formation of toxic by-products, is the subject matter of the present application.

SUMMARY OF THE INVENTION

A first aspect of the present invention relates to an enzyme isolated from an extremophilic microbe that displays optimum enzymatic activity at a temperature of greater than about 80° C., and a pH of less than about 2.

Another aspect of the present invention relates to a hemicellulase that was derived from *Alicyclobacillus acidocaldarius* (ATCC 27009).

Another aspect of the present invention relates to an enzyme that is useful in the hydrolysis of polysaccharides.

Still further, another aspect of the present invention relates to an enzyme that may be useful in a simultaneous saccharification and fermentation process to convert a biomass sugar into an end product.

Yet another aspect of the present invention relates to a method for the treatment of a biomass that includes the steps of providing a source of a biomass having a biomass sugar; pretreating the biomass with a water soluble hemicellulase derived from *Alicyclobacillus acidocaldarius* (ATCC 27009) to produce an end product.

Another aspect of the present invention relates to a method for the preparation of a hemicellulase that includes the steps of providing a source of *Alicyclobacillus acidocaldarius* (ATCC 27009); cultivating the *Alicyclobacillus acidocaldarius* (ATCC 27009) in a microbial nutrient medium having a supernatant; separating the cells of the *Alicyclobacillus acidocaldarius* from the nutrient medium supernatant; and recovering and purifying the hemicellulase derived from the *Alicyclobacillus acidocaldarius* (ATCC 27009) from the nutrient medium supernatant.

Moreover, another aspect of present invention relates to a method for hydrolyzing a polysaccharide that includes the steps of providing a water soluble hemicellulase derived from a microbe; and conducting hydrolysis of a polysaccharide with the water soluble hemicellulase at a pH of less than about 2.

These and other aspects of the present invention will be described in greater detail hereinafter.

BRIEF DESCRIPTION OF THE DRAWINGS

Preferred embodiments of the invention are described below with reference to the following accompanying drawings.

DETAILED DESCRIPTION OF THE PREFERRED EMBODIMENTS

This disclosure of the invention is submitted in furtherance of the constitutional purposes of the U.S. Patent Laws "to promote the progress of science and useful arts" (Article 1, Section 8).

The present invention, as described hereinafter, relates to an enzyme isolated from an extremophilic microbe that displays optimum enzymatic activity at a temperature of greater than about 80° C., and an optimum pH of less than about 2. In the present invention, the enzyme is a hemicellulase and/or xylanase that was derived from *Alicyclobacillus acidocaldarius*, where the organism is further identified as ATCC 27009. The enzyme, as discussed hereinafter, appears to display enzymatic activity at a pH of about 1. Still further, this same enzyme has a molecular weight of at least about 120 kDa. In the present invention, the enzyme, as disclosed, may be useful in a simultaneous saccharification and fermentation process and/or a sequential hydrolysis and fermentation process to convert a biomass sugar into an end product. Still further, the enzyme, as described herein, may be useful in the pretreatment of a biomass slurry to degrade a water-soluble or water insoluble oligomer and/or polysaccharide that is present in the biomass slurry to produce an end product.

As used hereinafter, the term "extremophilic microbe" means an organism that can live and thrive under conditions that humans would consider extreme, such as boiling water, ice, battery acid or at the bottom of the ocean. Examples of such microbes include, but are not limited to, *Pyrolobus fumarii* that grows at temperatures up to 235° F., *Psychrobacter cryopegella* that survives at temperatures of −20° C. (−4° F.), *Deinococcus radiodurans* that can survive in a nuclear reactor, *Photobacterium profundum* that thrives at pressures 300 times the atmospheric pressure at sea level, and *Picrophilus torridus* that lives at a pH of 0, the same as battery acid. Environments in which these microbes can be found include boiling hot springs, deep ocean thermal vents, glaciers, salt flats, and nuclear reactors. The microbes used in the present invention can be obtained from natural and artificial sources or commercially from culture depositories. In the present invention, the cultivation is preferably conducted at temperatures above 40° C. and a pH below about 5, and more preferably above 50° C. and below a pH 4, and most preferably above 55° C. and below a pH of 3.5, and under aerobic conditions. While the cultivation period varies depending upon the pH, temperature and nutrient medium used, a period of 12 hours to several days will generally give favorable results. As used herein, *Alicyclobacillus acidocaldarius* is defined as a microorganism that can be obtained from the American Type Culture Collection (ATCC), Manassas, Va., and that is identified as *Alicyclobacillus acidocaldarius* (ATCC 27009).

As used hereinafter, the phrase "enzymatic activity" means the reaction an enzyme causes to occur. Enzymes are proteins produced by all living organisms that mediate, cause and/or promote reactions that change a chemical into another type of chemical without themselves being altered or destroyed. In the context of the present application, the word "optimum," when used in combination with the term "enzymatic activity," means the most favorable conditions that allow the enzyme to work the best and the fastest for a given end result. The optimum enzymatic activity may be affected by conditions that include temperature, pH, and salt concentrations.

As used hereinafter, the word "xylanase" means an enzyme that breaks apart hemicellulose by breaking the chemical bonds between the xylose sugars that make up the backbone of the hemicellulose molecule, or by breaking bonds between xylose sugars in the hemicellulose side chains.

The word "polysaccharide" as used hereinafter shall mean a chain of sugars (can be the same sugars or different sugars) that are linked together by chemical bonds. Polysaccharides can consist of straight chains of these sugars with or without side chains. Examples of polysaccharides include starch, pectin, cellulose, and hemicellulose.

The word "hydrolysis" in the context of this present application shall mean a chemical reaction in which water reacts with a molecule and breaks it into at least two pieces.

As used hereinafter, the phrase "biomass sugar" shall mean sugars that have come from the breakdown of biomass components, such as cellulose and hemicellulose. Examples of biomass sugars include, but are not limited to, glucose, xylose, galactose, mannose, and arabinose.

The phrase "simultaneous saccharification and fermentation process" shall mean hereinafter a process for making a fuel or chemical such as ethanol from a biomass that may or may not have been pretreated by chemical means, and where cellulase and/or hemicellulase enzyme(s) are used to break down biomass polysaccharides into sugars (saccharification); and the sugars are fermented by source(s) of microorganism(s) into the product fuel or chemical (fermentation). These two processes occur at the same time, in the same reaction vessel (simultaneous).

The phrase "end product" as used in the present application shall mean hereinafter the chemical(s) that is/are produced by a chemical or enzymatic reaction. An example of an end product contemplated by the present invention includes xylose and/or one to several xylose molecules depending upon the treatment time and reaction conditions.

The word "biomass" in the context of the present invention shall mean plant and other cellulosic material such as corn stalks, wheat straw, and wood by-products, such as sawdust and the like.

The phrase "pretreatment of a biomass slurry" shall mean, in the context of the present application, the preparation of a biomass for its subsequent conversion to fuels, such as ethanol. This pretreatment includes the steps of grinding the biomass to a powder or small particles, and adding water (this constitutes a slurry). This slurry is then treated by a number of methods designed to partially or completely remove the lignin from the biomass, and convert the hemicellulose and cellulose into a form that can be more easily degraded into their component sugars using enzymes such as cellulases and hemicellulases. Some pretreatments degrade hemicellulose to its component sugars while leaving the cellulose as part of the solid residue. This treatment step is called a "pretreatment" because it occurs before both the enzymatic degradation step and before the fermentation step that converts the sugars into ethanol.

The phrase "water soluble" in the context of the present invention shall mean a chemical or other substance that can be dissolved completely in water without leaving any solid residue.

The word "hemicellulose" in the context of the present invention means one component of a plant (the other two being cellulose and lignin), that is made of a linear chain of sugars such as xylose, and mannose that are connected by a chemical bond. This linear chain also has branches consisting of sugars and other chemicals along the chain.

The word "hemicellulase" in the context of the present invention means a class of enzymes that can break hemicellulose into its component sugars. Examples of hemicellulases include xylanases, mannanases, glucuronidases, and arabinofuranosidases.

The phrase "sequential hydrolysis and fermentation process" in the context of the present invention shall mean a process for making a fuel or chemical from the biomass, such as ethanol, and where the biomass is treated at high temperature, and with acid (hydrolysis) to remove the lignin, and to convert the cellulose and hemicellulose present in the biomass into their component sugars or into a form that can be more easily degraded into their component sugars using enzymes such as cellulases and hemicellulases. These sugars, which are dissolved in water, are then cooled, and the pH adjusted to neutral, and then subsequently fermented by microorganisms of various types into a product fuel(s) or chemical(s) (fermentation). These two processes occur in separate reaction vessels with the hydrolysis step conducted first, and the fermentation step conducted second (sequential).

The phrase "cultivating *Alicyclobacillus acidocaldarius*" in the context of the present invention shall mean providing the aforementioned microbe with a food source (soluble or insoluble hemicellulose) and various vitamins and minerals dissolved in water (this constitutes the nutrient medium), and giving the microbe the proper conditions that allow it to grow (a temperature of 140° F., a pH of 3.5, and oxygen).

The phrase "separating the cells of the *Alicyclobacillus acidocaldarius*" in the context of the present invention shall include means for removing the bacterial cells from the nutrient medium by a process called centrifugation. In centrifugation, the cells and nutrient medium are put in tubes and spun in a circle. This is the same effect that is experienced on a merry-go-round where you feel pushed toward the outside. In a similar manner, the cells are pushed to the bottom of the tube and can be removed from the nutrient medium.

The phrase "recovering and purifying the hemicellulase" in the context of the present invention shall mean separating the hemicellulase enzyme from the nutrient medium. In the present invention, a process called cation exchange was used to separate hemicellulase from the nutrient medium. In this regard, the nutrient medium (with hemicellulase) was pumped through the cation exchange material. When brought into contact with the cation exchange material, the hemicellulase will attach itself to the cation exchange material, but the nutrient medium will pass through. The hemicellulase enzyme is then removed from the cation exchange material and is purified.

The phrase "microbial nutrient medium" in the context of the present application means a food source for the microbe (Alicyclobacillus acidocaldarius) and vitamins and minerals, all dissolved in water and adjusted to the pH needed by the microbe to grow. More specifically, the microbial nutrient medium includes about 1 gram per liter of Xylan; about 10 mM $NH_4Cl$; about 5.2 mM $K_2HPO_4$; about 0.8 mM $MgSO_4$-7 $H_2O$; about 1.74 mM $Na_2SO_4$; about 25 mg. per liter $MgCl_2$; about 6.6 mg. per liter of $CaCl_2$; about 2.0 mg. per liter $MnSO_4$; about 0.5 mg. per liter $ZnSO_4$; about 0.5 mg. per liter of boric acid; about 5 mg. per liter of $FeCl_3$; about 0.15 mg. per liter of $CuSO_4$; about 0.025 mg. per liter of $NaMoO_4$; about 0.05 mg. per liter of $CoNO_3$; about 0.02 mg. per liter of $NiCl_2$; about 0.08 mg per liter of pyridoxine hydrochloride; about 0.01 mg. per liter of folic acid; about 0.1 mg. per liter of thiamine hydrochloride; about 0.04 mg. per liter of riboflavin; about 0.08 mg. per liter of nicotinamide; about 0.08 mg. per liter of p-aminobenzoate; about 0.01 mg. per liter of biotin; about 0.0004 mg. per liter cyanocobalamin; about 0.08 mg. per liter D-pantothenic acid-Ca; about 0.02 mg. per liter of myo-inositol; about 0.05 mg. per liter of choline bromide; about 0.02 mg per liter of monosodium orotic acid; and about 0.1 mg. per liter spermidine, wherein the resulting nutrient medium is adjusted to a pH of about 3.5.

The word "supernatant" in the context of the present application shall mean the nutrient medium that is leftover after the bacterial cells are substantially removed from same.

The inventors have isolated and characterized temperature and acid stable xylanases that demonstrate activity at elevated temperatures, and low pH, and that show stability when incubated under these conditions for extended periods of time. The inventors recognize that heat and acid stable hemicellulases and cellulases, as described hereinafter, have particular value in, or as an accessory to, processes that would lead, on the one hand, to the reduction in the severity of pretreatment processes, earlier described, and/or the elimination of these limitations in various processes. In this regard, the inventors screened numerous organisms from Yellowstone National Park and various culture collections for microbes that had the ability to produce enzymes that were stable at both high temperature, and low pH. In this regard, water and sediment samples were collected from six springs in the Norris Geyser Basin of Yellowstone National Park. These samples were inoculated into a liquid mineral salt medium having a pH 3.5, and further containing either 0.5 grams per liter of oat spelt xylan, or 0.5 grams per liter of ground corn cobs. The subsequent cultures were incubated at 80° C. and were observed daily for growth, both visually and microscopically. Still further, a search of the American Type Culture Collection (ATCC) and the Deutsche Sammlung von Mikroorganismen Und Zellkulturen (DSMZ) yielded four possible heterotrophic organisms whose optimal temperatures, and pH, for growth, were greater than about 60° C., and less than about a pH of 4. These several organisms were grown in the media recommended by ATCC or DSMZ with a carbon source replaced by either oat spelt xylan, or ground corn cobs, as described above. These cultures where then later incubated at their optimum growth temperature and a pH of 3.5. Subsequent microbial growth was assessed visually by the appearance of turbidity.

In this investigation, hemicellulase and/or cellulase activities were presumptively assumed present if growth occurred in the presence of Xylan. Cultures where growth occurred were harvested after approximately three days incubation. Cells were removed from the culture by centrifugation. The culture supernatant was concentrated at about 1000-2000 fold using an AMICON® ultrafiltration cell with a 10,000 MWCO membrane. The subsequent supernatant concentrate was then tested for hemicellulase and cellulase activity using arsenomolybdate reducing sugar acid assay (previously described by Somogyi (1952), J. Biol. Chem. 195:19-23) with wheat arabinoxylan (commercially secured from Megazyme), or carboxymethylcellulose (secured from Sigma-Aldrich). These were used as substrates for the hemicellulase and cellulase activities, respectively. Standard conditions for the assays were set at 60° C., and a pH of about 3.5. As will be seen by reference to the drawings, the hemicellulase and cellulase activities were measured at temperatures up to about 90° C. to determine the optimum temperature for enzymatic activity. The reducing sugar assay referenced above was modified by changing the incubation temperature of the supernatant concentrate with the substrate. Similarly, the enzyme activities were measured at a pH ranging from 1 to about 8 to determine the optimum pH for the enzyme activity. For these studies, the reducing sugar assay was modified by preparing the assay components in the appropriate pH buffer (pH 1-2, 50 mM sodium maleate or 50 mM glycine; pH 2-6, 50 mM sodium acetate; pH 6-8, 50 mM sodium phosphate; and pH 8-9, 50 mM Tris).

In addition to the foregoing, the hemicellulase and cellulase's stabilities as a function of temperature and pH were examined by incubating the supernatant concentrate at a temperature of about 70° C., and a pH of 2.0. In this regard, a layer of mineral oil was placed over the concentrate to limit evaporation during this exam. Samples were periodically collected and assayed for hemicellulase and cellulase activity at the standard assayed conditions earlier described. With respect to the hemicellulase and cellulase reaction kinetics, these were determined using the reducing sugar assay with varying amounts of wheat arabinoxylan or carboxymethylcellulose. The reaction kinetics were determined at 60° C. and a pH of 3.5. Michaelis-Menten parameters $V_{MAX}$ and $K_M$ were calculated by nonlinear analysis using ENZYME KINETICS PRO™ that is available through SynexChem. After the process noted above, the inventors identified Alicyclobacillus acidocaldarius (ATCC 27009) for further examination.

Figure 1:
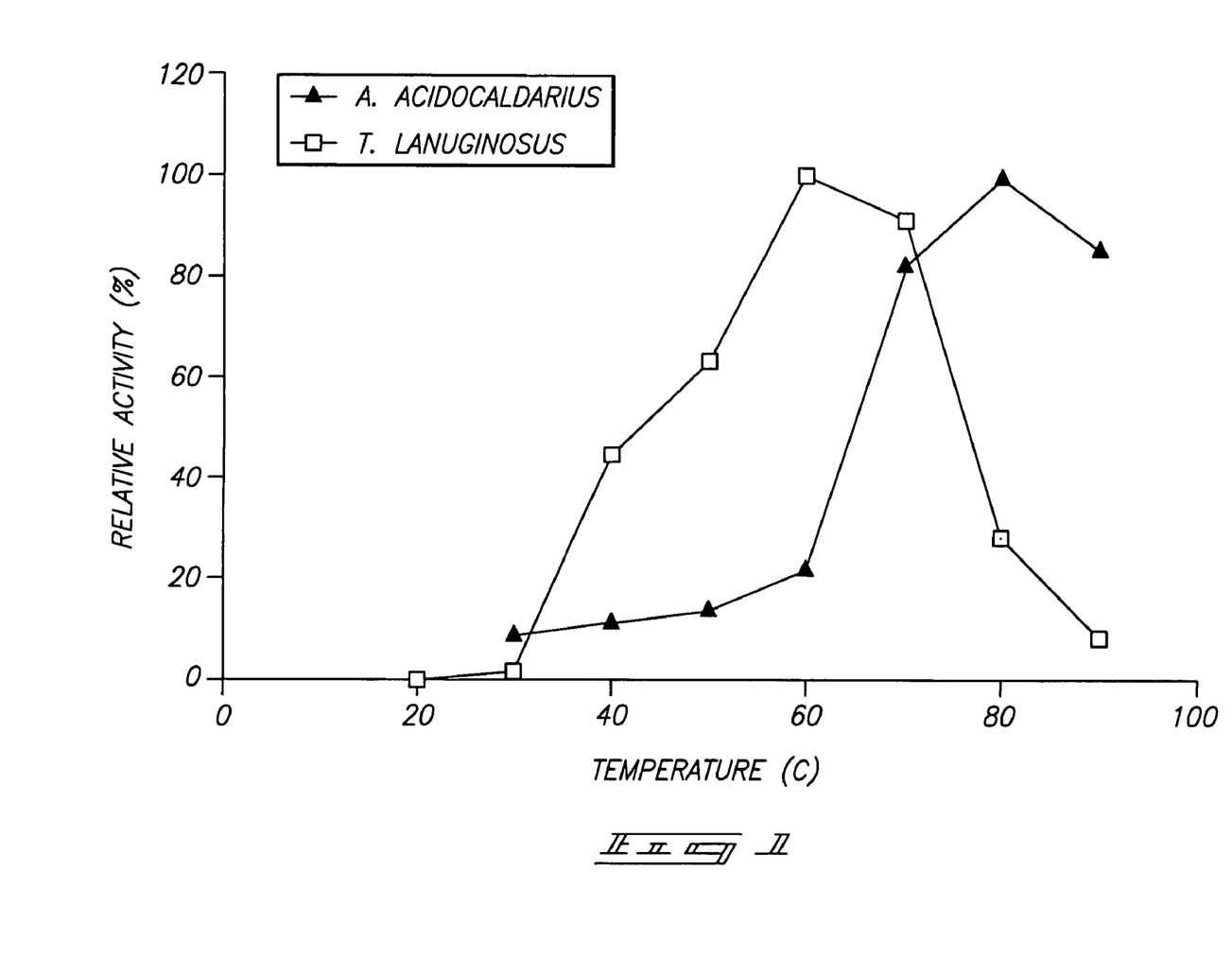
FIG. 1 is a graphical depiction of the effect of temperature on the xylanase activity as provided by the present invention.
Figure 2:
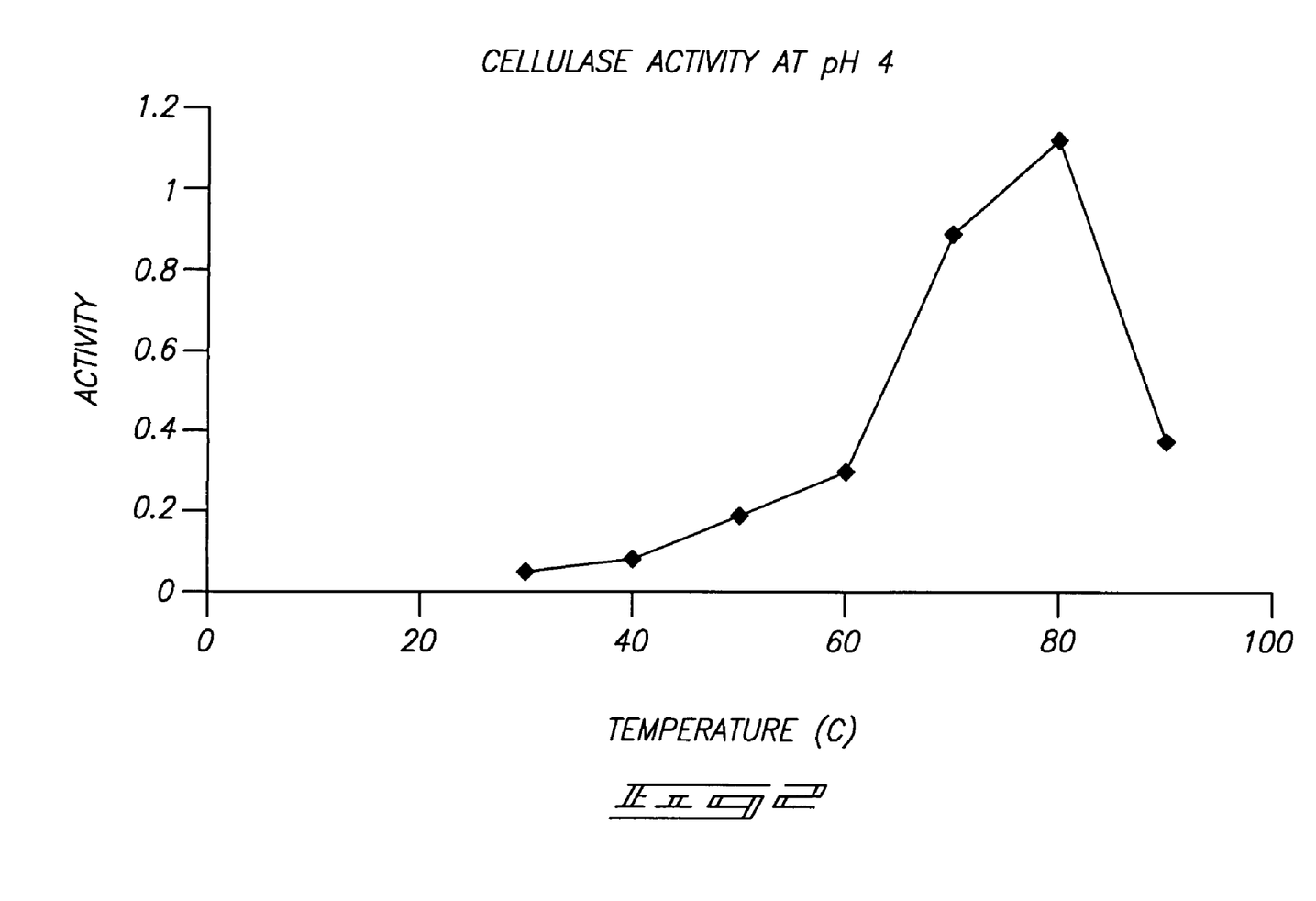
FIG. 2 is a graph depicting an effect of temperature on cellulase activity, as provided by the present invention at a pH of 4.0.
Figure 3:
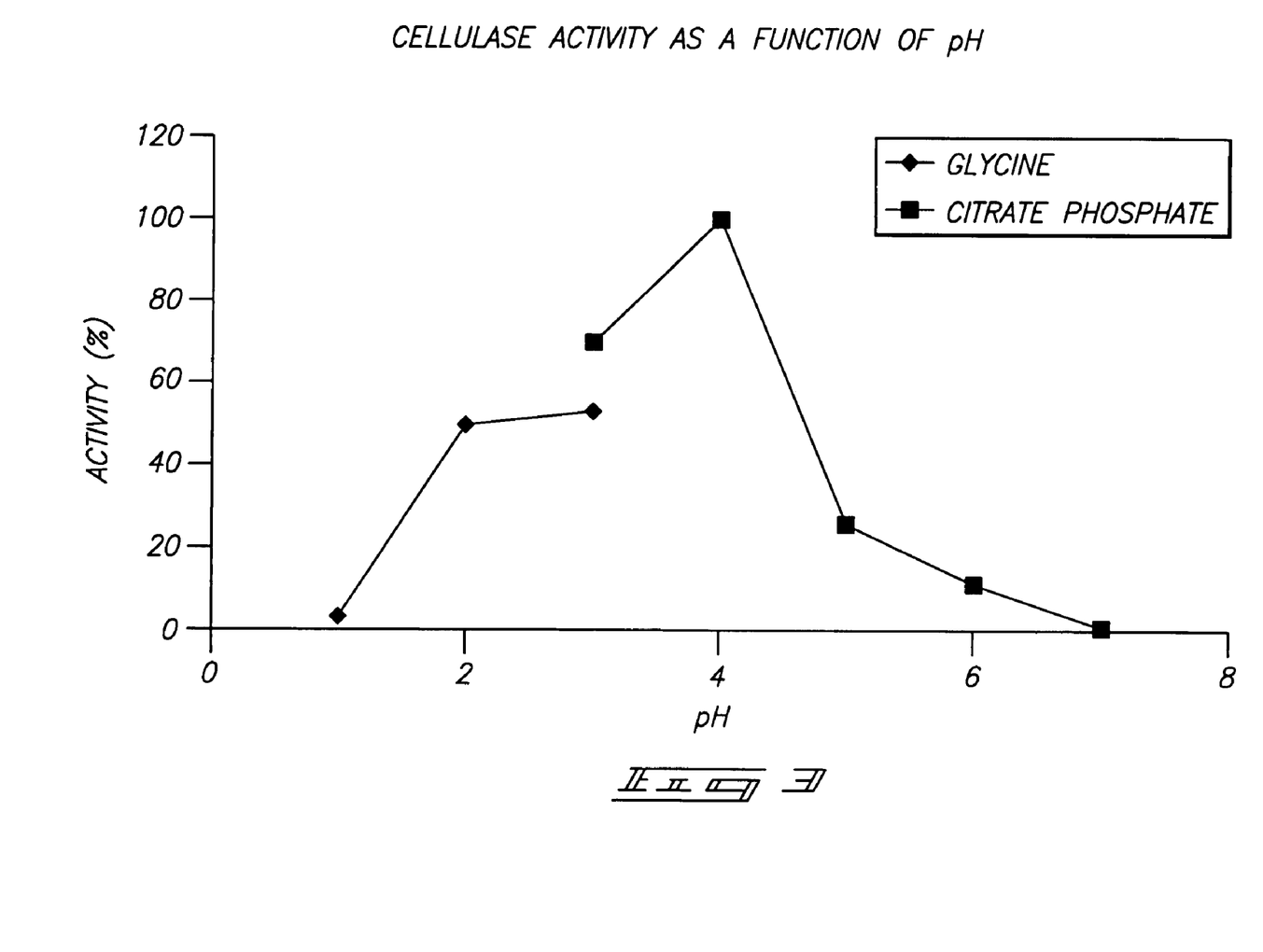
FIG. 3 is a graph depicting an effect of pH on cellulase activity of the present invention at a temperature of 60° C.
Figure 4:
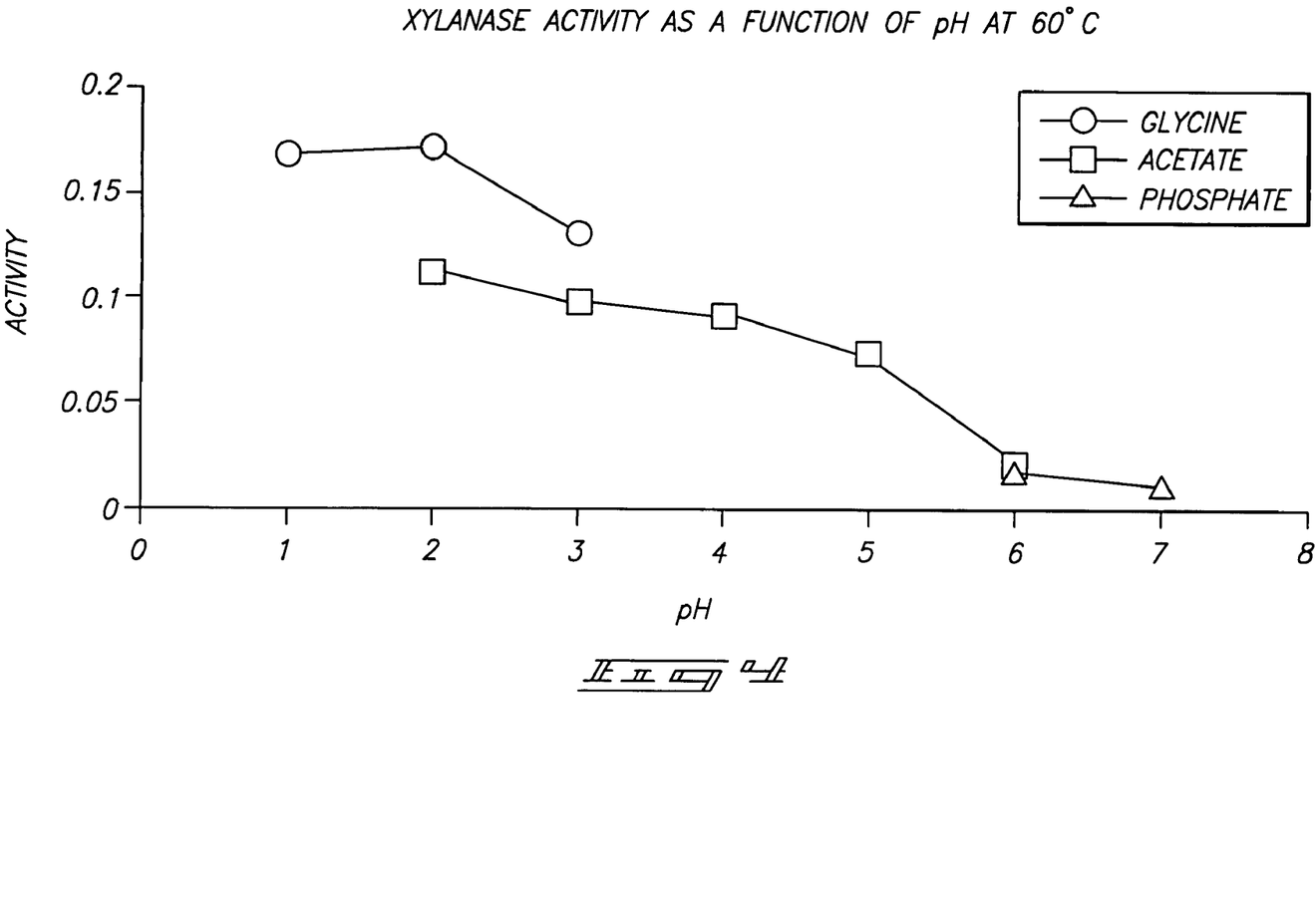
FIG. 4 is a graph depicting an effect of pH on xylanase activity of the present invention at a temperature of 60° C.

Subsequently, a crude enzyme preparation was made by concentrating the cell free culture material. A subsequent SDS-page gel showed five major bands and several minor bands. The subsequently calculated masses of these bands were consistent with other reported xylanases and cellulases. As seen in FIGS. 1, 2, 3 and 4, the inventors discovered that the enzyme isolated from the Alicyclobacillus acidocaldarius, which is identified herein as ATCC 27009, had an optimum temperature for enzymatic activity (xylanase and cellulase) at about 80° C. As seen in FIG. 1, the relative enzymatic activity is contrasted against the enzymatic activity that is provided by a similar enzyme that is isolated from another similar microbe T. lanuginosus. Further, it was found that the isolated xylanase exhibited enzymatic activity at a pH as low as 1, with an optimum pH of 2, while the optimum pH for the cellulase activity was at a pH of about 4, although it did show some activity at a pH as low as 2. FIG. 4 shows the xylanase activity as a function of pH as described above. To the best knowledge of the inventors, the lowest optimum hemicellulase pH previously reported was in the reference to Collins (2005, FEMS, Micro. Review, 29(1):3-23). It is conceivable that the present water soluble xylanase enzyme that has been isolated perhaps has activity at a pH lower than 1, however, presently, the reducing sugar assay reagents were unstable below a pH of 1. Further investigation revealed that the newly isolated hemicellulase and cellulase activities showed no decrease in activity when incubated at 70° C. and a pH of 2. The aforementioned investigation lead the inventors to conclude that the *Alicyclobacillus acidocaldarius* (ATCC 27009) is capable of growth on a xylan substrate, and further produces extracellular hemicellulase and cellulase activity, which are both water soluble and display significant hemicellulase activity at a pH of about 2, and which further has a molecular weight of at least about 120 kDa. Again, see FIG. 4.

The prior art discloses that an acid stable xylanase has been purified and characterized from *Aspergillus kawachii* that has a pH optimum of 2.0 and a temperature optimum between 50° C. to 60° C. (Purification and properties of acid stable xylanases from *Aspergillus kawachii*, K. Ito, H. Ogasawara, T. Sugomoto, and T. Ishikawa, Bioscience Biotechnology and Biochemistry 56 (4):547-550, April 1992.) Additionally, several xylanases have been reported with pH optima in the range of 4 to 5, and numerous xylanases have been reported that have temperature optima up to 100° C. However, in the inventors' knowledge, the enzyme as described hereinafter, is the first enzyme known that has activities at such a low pH, and at such a high temperature, as claimed herein. In addition to the foregoing, the inventors are aware that an endoglucanase has been purified from the same organism, that is, *Alicyclobacillus acidocaldarius* (ATCC 27009), that is reported to have xylanase activity associated with it. It is reported that this enzyme had a pH optimum of 4.0, and a temperature optimum of about 80° C. In this regard, a thermoacidophilic endoglucanase (celB) from *Alicyclobacillus acidocaldarius* (ATCC 27009) displayed high sequence similarity to arabinofuranosidases belonging to Family 51 of glycoside hydrolases (K. Eckert and E. Snyder, European Journal of Biochemistry, 270 (17):3593-3602, September, 2003). The aforementioned cellulase precursor as described in this prior art reference is best understood by a study of SEQ ID NO:5, which is shown below:

```
  1 MKRPWSAALA ALIALGTGAS PAWAAAHPSP KVPAGAAGRV
    RAADVVSTPI

51 SMEIQVIHDA LTVPELAAVQ AAAQAASNLS TSQWLQWLYP
    NATPTTSAQS

101 QAAQAVANLF NLATYGAVST RGSNAAQILQ TLQSISPLLS
    PRAVGLFYQS

151 FLTEIGQSSK AILARQASSS IVGNALAQAA SLSPTISAYL
    RQNGLSPSDL

201 ARTWSSFETQ VDPQGAAQTA LATRICTNAL GFGAPTASAT
    ITVNTAARLR

251 TVPATAFGLN AAVWDSGLNS QTVISEVQAL HPALIRWPGG
    SISDVYNWET

301 NTRNDGGYVN PNDTFDNFMQ FVNAVGASPI ITVNYGTGTP
    QLAADWVKYA

351 DVTHHDNVLY WEIGNEIYGN GYYNGNGWEA DDHAVPNQPQ
    KGNPGLSPQA

401 YAQNALQFIQ AMRAVDPNIK IGAVLTMPYN WPWGATVNGN
    DDWNTVVLKA

451 LGPYIDFVDV HWYPETPGQE TDAGLLADTD QIPAMVAELK
    REINAYAGSN

501 AKNIQIFVTE TNSVSYNPGQ QSTNLPEALF LADDLAGFVQ
    AGAANVDWWD

551 LLNGAEDNYT SPSLYGQNLF GDYGLLSSGQ ATPKGVQEPP
    QYTPLPPYYG

601 FQLVSDFARP GDTLLGSASS QSDIDVHAVR EPNGDIALML
    VNRSPSTIYS

651 ADLNVLGVGP YAITKALVYG EGSSAVSPAL TLPTAHSVKL
    MPYSGVDLVL

701 HPLIPAPHAA ASVTDTLALS SPTVTAGGSE TVTASFSSDR
    PVRDATVELE

751 LYDSTGDLVA NHEMTGVDIA PGQPVSESWT FAAPAANGTY
    TVEAFAFDPA

801 TGATYDADTT GATITVNQPP AAKYGDIVTK NTVITVNGTT
    YTVPAPDASG

851 HYPSGTNISI APGDTVTIQT TFANVSSTDA LQNGLIDMEV
    DGQNGAIFQK

901 YWPSTTLLPG QTETVTATWQ VPSSVSAGTY PLNFQAFDTS
    NWTGNCYFTN

951 GGVVNFVVN
```

With respect to the present invention, the new enzyme that was isolated from an extremophillic microbe has an N-terminal sequence comprising SEQ ID NO:1 as shown below:

DVVSTPISMEIQV.

It will be noted, that this N-terminal sequence of the present enzyme aligns/corresponds to positions 44-56 of SEQ ID NO:5.

In the present invention, an enzyme as contemplated by the present invention and that is isolated from an extremophilic microbe comprises that which is seen in SEQ ID NO:2, which is provided below:

QASSSIVGNALAQAASLSPTISAYLRQNGLSPSDLARTWSSYYCTQFDDP

QGAAQTALATRICNDQALGGGAPTASATITVNTAAR.

As should be understood, this SEQ ID NO:2 aligns/corresponds to positions 166-248 of the celB sequence as seen in SEQ ID NO:5. It should be noted, that SEQ ID NO:2 includes changed amino acids at position 207, 208, 212, 229, and 231; and added amino acids at position 209, 213, and 230, respectively.

In the present invention, the enzyme of the present invention may be further characterized, and is best understood by a study of SEQ ID NO:3 below:

GLNAAVWDSGLNSQTVISEVQALHPALIRWPGGSISDMDYNWETNTR

As should be understood SEQ ID NO:3, aligns/corresponds to position 258-304 of SEQ ID NO:5. It should be noted that SEQ ID NO:3 has a changed amino acid at position number 295, and an additional amino acid at position 296.

In the present invention, the enzyme as contemplated by the present invention further comprises the SEQ ID NO:4 as seen below:

EADDHAVPNQPQKGNPGLSPQAYAQNALQFMQSPVVYYR.

SEQ ID NO:4 aligns/corresponds to positions 379-415 of SEQ ID NO:5. It should be understood that with respect to the earlier SEQ ID NO:5, the present SEQ ID NO:4 has changes in amino acids at positions 409, 411, and 413, respectively. Still further, additional amino acids are located at positions 412 and 414-415, respectively.

In the prior art reference noted above to Eckert and Schneider, it is observed at page 3596 of the same publication that work had been conducted on the *Alicyclobacillus acidocaldarius* (ATCC 27009) for purposes of determining the presence of extracellular thermoacidophilic enzymes with polysaccharide-degrading activities. The authors noted that the organism was found to utilize a variety of polysaccharides including xylan as a sole source of carbon and energy. However, the authors failed to detect xylanase activity in the culture supernatant. The authors assumed a cell-associated enzyme and succeeded in extracting cellulose degrading activity with associated xylan degrading activity from the intact cells with Triton X-100. The authors observed that the cellulose degrading activity and its associated xylanase activity remained cell bound even after the culture reached the stationary phase of growth. In contrast, the enzyme isolated from the extremophilic microbe of the present invention that displays optimum enzymatic activities at temperatures equal to or greater than 80° C. and at a pH of less than 2, is considered to be water soluble, and further has been isolated from cell supernatant.

The present invention is also directed to a method for the preparation of a hemicellulase that includes the steps of providing a source of *Alicyclobacillus acidocaldarius* (ATCC 27009); cultivating the *Alicyclobacillus acidocaldarius* (ATCC 27009) in a microbial nutrient medium having a supernatant; separating the cells of the *Alicyclobacillus acidocaldarius* from the nutrient medium supernatant; and recovering and purifying the hemicellulase derived from the *Alicyclobacillus acidocaldarius* (ATCC 27009) from the nutrient medium supernatant. The methodology, as described, produces a hemicellulase that is water soluble and displays significant enzymatic activity at a pH of less than about 2, and at temperatures greater than about 80° C. In the methodology as described, the hemicellulase comprises the sequence as depicted in SEQ ID NOs:1, 2, 3, and/or 4. Still further, and in the methodology as described, the nutrient medium that is utilized further includes about 1 gram per liter of Xylan, about 10 mM $NH_4Cl$, about 5.2 mM $K_2HPO_4$, about 0.8 mM $MgSO_4$-$7H_2O$, about 1.74 mM $Na_2SO_4$, about 25 mg per liter $MgCl_2$, about 6.6 mg per liter of $CaCl_2$, about 2.0 mg per liter $MnSO_4$, about 0.5 mg per liter $ZnSO_4$, about 0.5 mg per liter of boric acid, about 5 mg per liter of $FeCl_3$, about 0.15 mg per liter of $CuSO_4$, about 0.025 mg per liter of $NaMoO_4$, about 0.05 mg per liter of $CoNO_3$, about 0.02 mg per liter of $NiCl_2$, about 0.08 mg per liter of pyridoxine hydrochloride, about 0.01 mg per liter of folic acid, about 0.1 mg per liter of thiamine hydrochloride, about 0.04 mg per liter of riboflavin, about 0.08 mg per liter of nicotinamide, about 0.08 mg per liter of p-aminobenzoate, about 0.01 mg per liter of biotin, about 0.0004 mg per liter cyanocobalamin, about 0.08 mg per liter D-pantothenic acid-Ca, about 0.02 mg per liter of myo-inositol, about 0.05 mg per liter of choline bromide, about 0.02 mg per liter of monosodium orotic acid, and about 0.1 mg per liter spermidine, and wherein the resulting nutrient medium is adjusted to a pH of about 3.5. As discussed earlier in the application, the present enzyme may be used in various processes. Therefore the methodology as described above includes the step of supplying the recovered and purified hemicellulase to a simultaneous saccharification and fermentation process to facilitate the conversion of a biomass polysaccharides into an end product. One process for using the enzyme as noted above includes a step of pretreating a biomass slurry with the recovered and purified hemicellulase or with a crude enzyme preparation prepared from the organism containing a majority of the protein comprised of the hemicellulase to degrade an oligomer and/or polysaccharide that is present in the biomass slurry to produce an end product.

Other possible methods for using the enzyme as described above may be employed. For example, the enzyme that has been isolated from the extremophilic microbe may be used in a method for hydrolyzing a polysaccharide, which includes the step of providing a water soluble hemicellulase derived from an extremophilic microbe; and conducting hydrolysis of a polysaccharide with the water soluble hemicellulase at a pH of less than about 2. As was discussed, earlier, the water soluble hemicellulase has an optimal enzymatic activity at temperatures of about 80° C.

Operation

The operation of the described embodiment of the present invention is believed to be readily apparent and is briefly summarized at this point.

As described, an enzyme isolated from extremophilic microbe that displays optimum enzymatic activity at a temperature of about 80° C. and a pH of less than about 2 is best understood by a study of SEQ ID NOs:2-4, respectively. The enzyme that has been isolated is useful in a method for treating a biomass, which includes the steps of providing a source of a biomass having a biomass sugar; pretreating the biomass with a water soluble hemicellulase derived from *Alicyclobacillus acidocaldarius* (ATCC 27009) to produce an end product. In the present methodology, the biomass sugar comprises a polysaccharide, and the hemicellulase hydrolyzes the polysaccharide. As discussed above, the hemicellulase displays enzymatic activity at a pH of less than about 2, and at temperature of greater than about 80° C.

The hemicellulase, as contemplated by the present invention, has a molecular weight of about 120 kDa. In the methodology as described above, the methodology includes additional steps of pretreating the biomass in the presence or absence of the hemicellulase; providing a sequential hydrolysis and fermentation process to convert the biomass sugar into the end product; and supplying the hemicellulase to the sequential hydrolysis and fermentation process to facilitate the conversion of the biomass sugar into the end product. After the step of pretreating the biomass as discussed above, which can be performed at reduced severity in the presence or absence of the hemicellulase, the method includes a further step of providing a simultaneous saccharification and fermentation process to convert the biomass sugar into the end product; and supplying the hemicellulase to the simultaneous saccharification and fermentation process to facilitate the conversion of the biomass sugar into the end product.

Therefore, it will be seen that the present enzyme and methodology, as described above, avoids many of the shortcomings attendant with the prior art enzymes and practices employed heretofore, and further provides a convenient means for producing various desirable end products, while simultaneously reducing the severity of pretreatment steps that had the propensity for generating various deleterious waste products, as well as for increasing the cost of the overall process through the requirement of high temperatures, pressures and quantities of acid to attain the high pretreatment severity.

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

We claim:

1. An isolated or purified enzyme wherein the enzyme displays optimum enzymatic activity at a temperature of greater than about 80° C., and at a pH of less than about 2, and wherein the enzyme is a hemicellulase or xylanase which was derived from *Alicyclobacillus acidocaldarius*.

2. The enzyme of claim 1, wherein the enzyme is water soluble.

3. The enzyme of claim 1, wherein the enzyme displays significant enzymatic activity at a pH of about 1.

4. The enzyme of claim 1, wherein the enzyme has a molecular weight of at least about 120 kDa.

5. The enzyme of claim 1, wherein the enzyme has a molecular weight which is at least 20% greater than the enzyme as set forth in SEQ ID NO:5.

6. The enzyme of claim 1, which is useful in a simultaneous saccharification and fermentation process to convert a biomass sugar into an end product.

7. The enzyme of claim 1, which is useful in a sequential hydrolysis and fermentation process to convert a biomass sugar into an end product.

8. The enzyme of claim 1, which is useful in a pretreatment of a biomass slurry to degrade an oligomer and/or polysaccharide which is present in the biomass slurry to produce an end product.

9. A method for the treatment of a biomass, comprising:
   providing an isolated or purified enzyme derived from *Alicyclobacillus acidocaldarius* wherein the enzyme displays optimum enzymatic activity at a temperature of greater than about 80° C., and at a pH of less than about 2, and where the enzyme is a hemicellulase or xylanase;
   providing a source of a biomass;
   treating the biomass with the enzyme of to produce an end product.

10. The method according to claim 9, wherein the treatment of the biomass comprises hydrolyzing a polysaccharide present in the biomass with the enzyme.

11. The method according to claim 9, wherein the enzyme has a molecular weight of about 120 kDa.

12. The method according to claim 9, wherein the treatment of the biomass comprises:
   a sequential hydrolysis and fermentation process to produce and convert biomass sugar into the end product;
   wherein the enzyme of is supplied to the sequential hydrolysis and fermentation process to facilitate the conversion of the biomass sugar into the end product.

13. The method according to claim 9, wherein the treatment of the biomass comprises:
   a simultaneous saccharification and fermentation process to produce and convert biomass sugar into the end product;
   wherein the enzyme of is supplied to the simultaneous saccharification and fermentation process to facilitate the conversion of the biomass sugar into the end product.

14. The method according to claim 9, wherein the treatment of the biomass comprises:
   degrading an oligomer and/or polysaccharide which is present in the biomass to produce an end product.

15. A method for the preparation of the enzyme of claim 1, the method comprising:
  providing a source of *Alicyclobacillus acidocaldarius*;
  cultivating the *Alicyclobacillus acidocaldarius* in a microbial nutrient medium having a supernatant;
  separating the cells of the *Alicyclobacillus acidocaldarius* from the nutrient medium supernatant; and
  recovering and purifying the enzyme of claim 1 from the nutrient medium supernatant.

16. The method according to claim 15, wherein the enzyme is water soluble.

17. The method according to claim 15, wherein the enzyme comprises SEQ ID NO:1.

18. The method according to claim 15, wherein nutrient medium further comprises:
  about 1 gram per liter of Xylan;
  about 10 mM $NH_4Cl$;
  about 5.2 mM $K_2HPO_4$;
  about 0.8 mM $MgSO_4$-7 $H_2O$;
  about 1.74 mM $Na_2SO_4$;
  about 25 mg per liter $MgCl_2$;
  about 6.6 mg per liter of $CaCl_2$;
  about 2.0 mg per liter $MnSO_4$;
  about 0.5 mg per liter $ZnSO_4$;
  about 0.5 mg per liter of boric acid;
  about 5 mg per liter of $FeCl_3$;
  about 0.15 mg per liter of $CuSO_4$;
  about 0.025 mg per liter of $NaMoO_4$;
  about 0.05 mg per liter of $CoNO_3$;
  about 0.02 mg per liter of $NiCl_2$;
  about 0.08 mg per liter of pyridoxine hydrochloride;
  about 0.01 mg per liter of folic acid;
  about 0.1 mg per liter of thiamine hydrochloride;
  about 0.04 mg per liter of riboflavin;
  about 0.08 mg per liter of nicotinamide;
  about 0.08 mg per liter of p-aminobenzoate;
  about 0.01 mg per liter of biotin;
  about 0.0004 mg per liter cyanocobalamin;
  about 0.08 mg per liter D-pantothenic acid-Ca;
  about 0.02 mg per liter of myo-inositol;
  about 0.05 mg per liter of choline bromide;
  about 0.02 mg per liter of monosodium orotic acid; and
  about 0.1 mg per liter spermidine, and wherein the resulting nutrient medium is adjusted to a pH of about 3.5.

19. A method for hydrolyzing a polysaccharide, comprising:
  providing the enzyme of claim 1; and
  conducting hydrolysis of a polysaccharide with the enzyme of claim 1.

20. An isolated or purified enzyme wherein the enzyme displays optimum enzymatic activity at a temperature of greater than about 70° C., and at a pH of less than about 3, and wherein the enzyme is a hemicellulase or xylanase which was derived from *Alicyclobacillus acidocaldarius*.

* * * * *

UNITED STATES PATENT AND TRADEMARK OFFICE
CERTIFICATE OF CORRECTION

PATENT NO. : 7,727,755 B2  
APPLICATION NO. : 11/266063  
DATED : June 1, 2010  
INVENTOR(S) : Vicki S. Thompson et al.

Page 1 of 1

It is certified that error appears in the above-identified patent and that said Letters Patent is hereby corrected as shown below:

In the specification:

| | | |
|---|---|---|
| COLUMN 2, | LINE 29, | change "graphical depiction of the" to --graph depicting an-- |
| COLUMN 2, | LINE 30, | change "on the xylanase activity as" to --on xylanase activity, as-- |

In the claims:

| | | | |
|---|---|---|---|
| CLAIM 9, | COLUMN 18, | LINE 41, | change "enzyme of to" to --enzyme to-- |
| CLAIM 12, | COLUMN 18, | LINE 52, | change "enzyme of is" to --enzyme is-- |
| CLAIM 13, | COLUMN 18, | LINE 60, | change "enzyme of is" to --enzyme is-- |

Signed and Sealed this  
Twenty-seventh Day of October, 2015

Michelle K. Lee  
*Director of the United States Patent and Trademark Office*